United States Patent
Junnarkar

(10) Patent No.: US 10,190,962 B2
(45) Date of Patent: *Jan. 29, 2019

(54) FLOW CYTOMETRY SYSTEMS AND METHODS FOR BLOCKING DIFFRACTION PATTERNS

(71) Applicant: Abbott Laboratories, Abbott Park, IL (US)

(72) Inventor: Mahesh R. Junnarkar, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 6 days.

This patent is subject to a terminal disclaimer.

(21) Appl. No.: 15/431,115

(22) Filed: Feb. 13, 2017

(65) Prior Publication Data

US 2017/0219476 A1   Aug. 3, 2017

Related U.S. Application Data

(63) Continuation of application No. 14/954,180, filed on Nov. 30, 2015, now Pat. No. 9,606,043, which is a (Continued)

(51) Int. Cl.
  *G01N 21/00*   (2006.01)
  *G01N 15/14*   (2006.01)
  *G01N 21/53*   (2006.01)

(52) U.S. Cl.
  CPC ..... *G01N 15/1434* (2013.01); *G01N 15/1459* (2013.01); *G01N 21/53* (2013.01);
(Continued)

(58) Field of Classification Search
  CPC .............. G01N 15/14; G01N 15/1404; G01N 15/0205; G01N 2015/1493; G01N 2015/1037; G01N 21/53; G01N 2021/4711
(Continued)

(56) References Cited

U.S. PATENT DOCUMENTS

| | | |
|---|---|---|
| 4,037,965 A | 7/1977 | Weiss |
| 5,125,737 A | 6/1992 | Rodriguez et al. |

(Continued)

FOREIGN PATENT DOCUMENTS

| | | |
|---|---|---|
| EP | 1250585 | 10/2002 |
| JP | S59176649 A | 10/1984 |

(Continued)

*Primary Examiner* — Hoa Pham
(74) *Attorney, Agent, or Firm* — Edward J. Baba; Payal B. Sud; Bozicevic, Field & Francis LLP

(57) ABSTRACT

Flow cytometer systems are provided having intermediate angle scatter detection capability. In some aspects, systems are provided that include an intermediate angle scatter (IAS) light detector positioned to measure intermediate angle scatter emitted from a flow cytometer. The system further includes a mask disposed across a portion of the IAS light detector and positioned between the flow cell and the IAS light detector to cover at least a central portion of the IAS light detector so as to block a diffraction pattern observed at the detector. In some instances, the diffraction pattern is created by a flat beam profile irradiating the sample. Methods are also provided for configuring a flow cytometer to block a diffraction pattern created by (1) a flat laser beam profile irradiating a flow cytometer liquid sample, or (2) a mismatched index of refraction between a sheath fluid and a liquid sample in a flow cytometer.

20 Claims, 2 Drawing Sheets

Related U.S. Application Data continuation of application No. 13/722,550, filed on Dec. 20, 2012, now Pat. No. 9,201,005.

(60) Provisional application No. 61/581,462, filed on Dec. 29, 2011.

(52) U.S. Cl.
CPC ............... *G01N 2015/1452* (2013.01); *G01N 2201/06113* (2013.01)

(58) Field of Classification Search
USPC .................................. 356/73, 335–343, 246
See application file for complete search history.

(56) References Cited

U.S. PATENT DOCUMENTS

| | | | |
|---|---|---|---|
| 5,461,476 A | 10/1995 | Fournier | |
| 5,631,165 A | 5/1997 | Chupp et al. | |
| 5,631,730 A | 5/1997 | Chupp et al. | |
| 6,084,670 A | 7/2000 | Yamazaki et al. | |
| 6,228,652 B1 | 5/2001 | Rodriguez et al. | |
| 6,606,157 B1 | 8/2003 | Kaye et al. | |
| 7,113,266 B1 | 9/2006 | Wells | |
| 7,576,857 B2 | 8/2009 | Wagner | |
| 8,094,299 B2 | 1/2012 | Wells et al. | |
| 8,189,187 B2 | 5/2012 | Graham et al. | |
| 8,339,585 B2 * | 12/2012 | Wells | G01N 15/147 356/337 |
| 8,906,308 B2 | 12/2014 | Krockenberger et al. | |
| 9,201,005 B2 * | 12/2015 | Junnarkar | G01N 21/53 |
| 9,606,043 B2 * | 3/2017 | Junnarkar | G01N 21/53 |
| 2004/0189977 A1 | 9/2004 | Nagai et al. | |
| 2006/0221325 A1 | 10/2006 | Wells | |
| 2007/0212262 A1 | 9/2007 | Rich | |
| 2008/0186490 A1 | 8/2008 | Chu | |
| 2011/0045525 A1 | 2/2011 | Krockenberger et al. | |
| 2014/0264097 A1 | 9/2014 | Heanue et al. | |
| 2014/0268102 A1 | 9/2014 | Shah | |

FOREIGN PATENT DOCUMENTS

| | | |
|---|---|---|
| JP | H01502533 A | 8/1989 |
| JP | H09508703 A | 9/1997 |
| JP | H1123447 A | 1/1999 |
| WO | WO 2010/011246 | 1/2010 |

\* cited by examiner

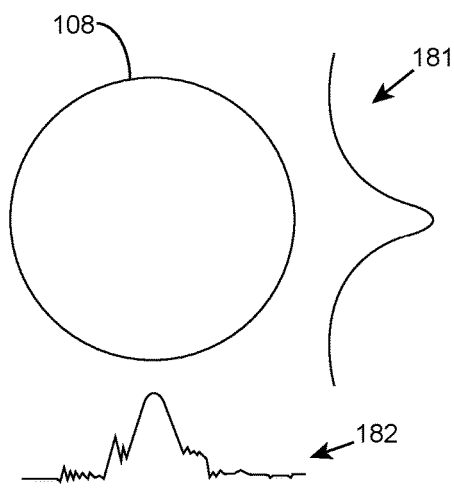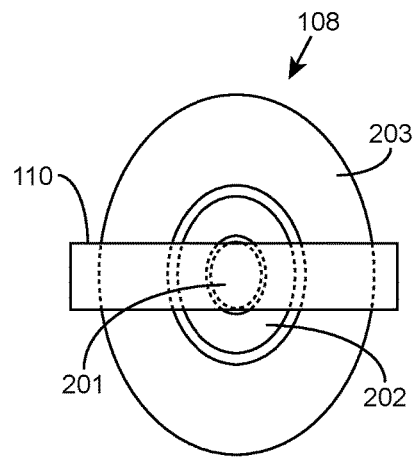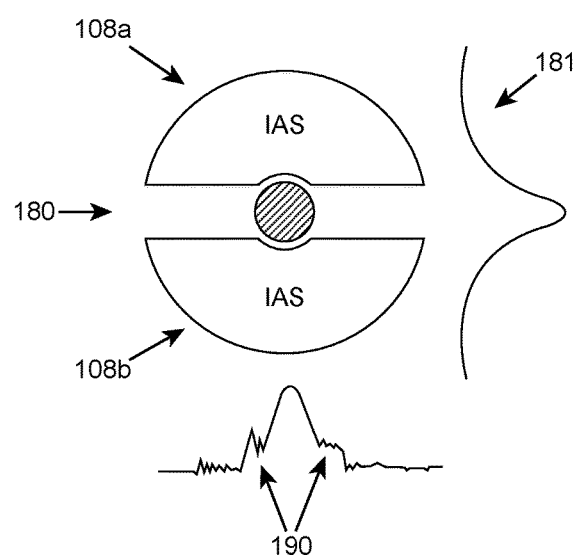

FLOW CYTOMETRY SYSTEMS AND METHODS FOR BLOCKING DIFFRACTION PATTERNS

This application is a continuation of U.S. patent application Ser. No. 14/954,180, filed on Nov. 30, 2015, issued as U.S. Pat. No. 9,606,043, which is a continuation of U.S. patent application Ser. No. 13/722,550, filed on Dec. 20, 2012, issued as U.S. Pat. No. 9,201,005, and claims priority to the filing date of U.S. Provisional Patent Application Ser. No. 61/581,462, filed on Dec. 29, 2011, the disclosures of which applications are herein incorporated by reference in their entirety.

BACKGROUND

A flow cytometer system is provided. The system includes a flow cell for streaming a hydro-dynamically focused liquid sample past an interrogation zone, a light source positioned to irradiate the interrogation zone with a light beam, and beam shaping optics disposed between the light source and the flow cell. The beam shaping optics manipulates the light beam and creates a horizontally flat beam profile that irradiates the liquid sample at the interrogation zone. The system includes an intermediate angle scatter (IAS) light detector positioned to measure intermediate angle scatter emitted from the liquid sample when the liquid sample is irradiated. The system further includes a mask disposed horizontally across a portion of the IAS light detector, between the flow cell and the IAS light detector, and covering at least a central portion of the IAS light detector so as to block a horizontal diffraction pattern created by the flat beam profile irradiating the liquid sample.

SUMMARY

The present disclosure generally provides a flow cytometer system including a flow cell for streaming a hydro-dynamically focused liquid sample past an interrogation zone, a light source positioned to irradiate the interrogation zone with a light beam, a plurality of beam shaping optics disposed between the light source and the flow cell, wherein the beam shaping optics manipulate the light beam and create a horizontally flat beam profile that irradiates the liquid sample at the interrogation zone, an intermediate angle scatter (IAS) light detector positioned to measure intermediate angle scatter emitted from the liquid sample when the liquid sample is irradiated, and a mask disposed horizontally across a portion of the IAS light detector and positioned between the flow cell and the IAS light detector to cover at least a central portion of the IAS light detector so as to block a horizontal diffraction pattern created by the flat beam profile irradiating the liquid sample.

In some embodiments, the light source is a laser.

In some embodiments, the flow cytometer further comprises a sheath fluid source for drawing a sheath fluid used to hydro-dynamically focus the liquid sample.

In some embodiments, the sheath fluid is water.

In some embodiments, the mask is selected from the group consisting of: a tape, an obstruction bar, and a photolithographic obstruction.

In some embodiments, the IAS light detector includes two concentric detector rings.

In some embodiments, the first detector ring measures intermediate angle scatter between about 2-7 degrees.

In some embodiments, the second detector ring measures intermediate angle scatter between about 7-11 degrees.

In some embodiments, the two concentric detector rings comprise a first concentric detector ring and a second concentric detector ring, and the IAS light detector includes a central detector ring disposed concentrically within the first and second concentric detector rings.

In some embodiments, the first concentric detector ring has an inner radius of approximately 4 mm and an outer radius of approximately 7.6 mm, and the second concentric detector ring has an inner radius of approximately 9.6 mm and an outer radius of approximately 13 mm.

In some embodiments, the mask is an obstruction bar.

In some embodiments, the obstruction bar is a holed mirror positioned to allow an axial light loss measurement through a central hole in the obstruction bar and to redirect intermediate angle scatter from the flow cell to the IAS light detector.

In some embodiments, the present disclosure provides a flow cytometer system including a flow cell for streaming a hydro-dynamically focused liquid sample past an interrogation zone, a sheath fluid source for drawing a sheath fluid used to hydro-dynamically focus the liquid sample, wherein the sheath fluid is water, a light source positioned to irradiate the interrogation zone with a light beam, a plurality of beam shaping optics disposed between the light source and the flow cell, wherein the beam shaping optics manipulate the light beam, an intermediate angle scatter (IAS) light detector positioned to measure intermediate angle scatter emitted from the liquid sample when the liquid sample is irradiated, and a mask disposed across a portion of the IAS light detector and positioned between the flow cell and the IAS light detector to cover at least a central portion of the IAS light detector so as to block a diffraction pattern created by the sheath fluid when the liquid sample is irradiated.

In some embodiments, the light source is a laser.

In some embodiments, the plurality of beam shaping optics creates a horizontally flat beam profile that irradiates the liquid sample at the interrogation zone.

In some embodiments, the mask is a tape, an obstruction bar, or a photolithographic obstruction.

In some embodiments, the IAS light detector includes two concentric detector rings.

In some embodiments, the first detector ring measures intermediate angle scatter between about 2-7 degrees.

In some embodiments, the second detector ring measures intermediate angle scatter between about 7-11 degrees.

In some embodiments, the two concentric detector rings include a first concentric detector ring and a second concentric detector ring, and the IAS light detector includes a central detector ring disposed concentrically within the first and second concentric detector rings.

In some embodiments, the first concentric detector ring has an inner radius of approximately 4 mm and an outer radius of approximately 7.6 mm, and the second concentric detector ring has an inner radius of approximately 9.6 mm and an outer radius of approximately 13 mm.

In some embodiments, the mask is an obstruction bar. In some embodiments, the obstruction bar is a holed mirror positioned to allow an axial light loss measurement through a central hole in the obstruction bar and to redirect intermediate angle scatter from the flow cell to the IAS light detector.

In some embodiments, the present disclosure provides a system for blocking a diffraction pattern created by a flat laser beam profile irradiating a flow cytometer liquid sample or a mismatched index of refraction between a sheath fluid and a liquid sample in a flow cytometer, the system including an intermediate angle scatter (IAS) light detector positioned to measure intermediate angle scatter emitted from the liquid sample when the liquid sample is irradiated, and a mask disposed across a portion of the IAS light detector and covering at least a central portion of the IAS light detector so as to block a diffraction pattern.

In some embodiments, the mask is disposed horizontally across the IAS light detector. In some embodiments, the mask is a tape, an obstruction bar, or a photolithographic obstruction.

In some embodiments, the IAS light detector further comprises two concentric detector rings. In some embodiments, the first detector ring measures intermediate angle scatter between about 2-7 degrees. In some embodiments, the second detector ring measures intermediate angle scatter between about 7-11 degrees. In some embodiments, the two concentric detector rings include a first concentric detector ring and a second concentric detector ring, and the IAS light detector includes a central detector ring disposed concentrically within the first and second concentric detector rings. In some embodiments, the first concentric detector ring has an inner radius of approximately 4 mm and an outer radius of approximately 7.6 mm, and the second concentric detector ring has an inner radius of approximately 9.6 mm and an outer radius of approximately 13 mm.

In some embodiments, the mask is an obstruction bar. In some embodiments, the obstruction bar is a holed mirror positioned to allow an axial light loss measurement through a central hole in the obstruction bar and to redirect intermediate angle scatter to the IAS light detector.

In some embodiments, the present disclosure provides a method of configuring a flow cytometer to block a diffraction pattern created by a flat laser beam profile irradiating a flow cytometer liquid sample, or a mismatched index of refraction between a sheath fluid and a liquid sample in a flow cytometer, the method involving positioning a mask across a portion of an intermediate angle scatter (IAS) light detector, which is positioned to measure intermediate angle scatter emitted from the liquid sample when the liquid sample is irradiated, wherein the mask covers at least a central portion of the IAS light detector so as to block a diffraction pattern.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the systems and methods presented. In the drawings, like reference numbers indicate identical or functionally similar elements.

FIG. 2 illustrates a diagram of scattered light signals in the vertical and horizontal directions, according to one embodiment.

FIG. 3 illustrates a diagram of a mask disposed on an IAS detector, according to one embodiment.

FIG. 4 illustrates a slotted detector, according to one embodiment.

DETAILED DESCRIPTION

Figure 1:
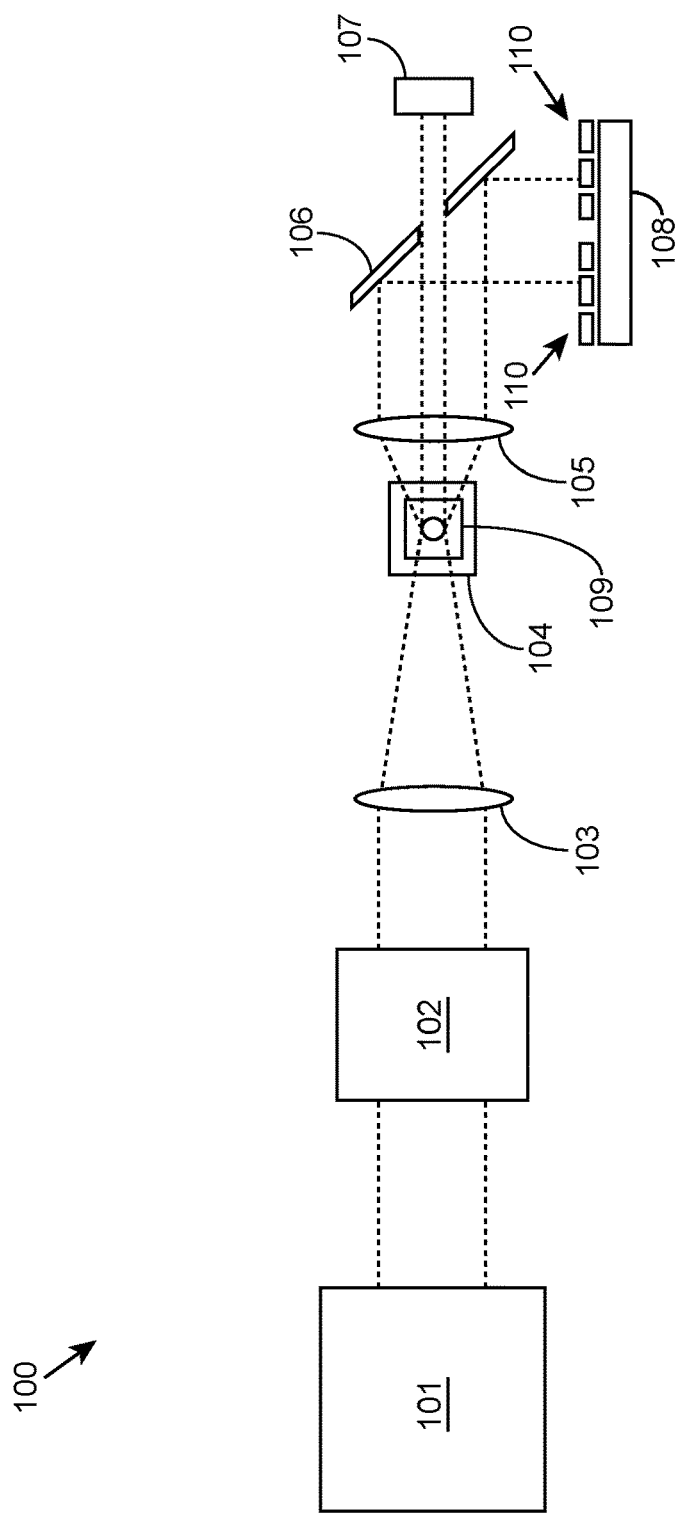
FIG. 1 illustrates a system block diagram of a flow cytometer system, according to one embodiment.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

The present disclosure relates generally to hematology instruments and detection of forward scatter in flow cytometers. In certain embodiments, the flow cytometer systems presented generally include: a flow cell for streaming a hydro-dynamically focused liquid sample past an interrogation zone; a light source positioned to irradiate the interrogation zone with a light beam; and beam shaping optics disposed between the light source and the flow cell. The beam shaping optics manipulates the light beam and creates a horizontally flat beam profile that irradiates the liquid sample at the interrogation zone. The systems may include an intermediate angle scatter (IAS) light detector positioned to measure intermediate angle scatter emitted from the liquid sample when the liquid sample is irradiated. Factors such as the differences in refractive index between the liquid sample and the sheath fluid may cause diffraction patterns or ripples at the IAS detectors. The flat-top beam profile (also referred to as "flat beam profile" herein) also may create diffraction patterns at the IAS detectors. Diffraction patterns contaminate the scatter signal and provide inaccuracies in the intermediate angle scatter measurement. As such, the systems may further include a mask disposed horizontally across a portion of the IAS light detector, between the flow cell and the IAS light detector, and covering at least a central portion of the IAS light detector so as to block a horizontal diffraction pattern created by the flat beam profile irradiating the liquid sample.

The present disclosure includes embodiments and description related to a "horizontal" flat-top beam profile—e.g., wherein the "horizontal" beam profile is a flat-top profile and the "vertical" beam profile is a Gaussian curve. It should be appreciated that the terms "horizontal" and "vertical" are used generally to provide relative axis orientations and to facilitate understanding. It should be understood that the underlying concepts and principles of the present disclosure are also applicable to other embodiments, wherein the "vertical" beam profile is a flat-top profile and the "horizontal" beam profile is a Gaussian curve.

FIG. 1 illustrates a system block diagram of a flow cytometer system, according to one embodiment. The system 100 includes: a light source 101, beam shaping optics 102, a focusing lens 103, a flow cell 104, a lens 105, a reflector 106, an axial light loss (ALL) detector 107, and an IAS detector 108. The light source 101 may be a laser, for example, and provides a laser beam into the beam shaping optics 102, which is positioned between the light source 101 and the flow cell 104. The laser light beam is manipulated by the beam shaping optics 102 to provide a shaped beam, and then focused by focusing lens 103 to hit an interrogation zone 109 of the flow cell 104. In other embodiments, the focusing lens 103 is not included, and the beam shaping optics 102 alone provides the appropriately shaped beam profile onto the interrogation zone 109.

In one embodiment, the beam shaping optics 102 manipulates the light beam to create a horizontally flat-top beam profile that irradiates the liquid sample at the interrogation zone 109. The beam shaping optics 102 may include, for example, a combination of lenses configured to produce a flat-top beam profile at the point of intersection with the interrogation zone 109. The beam shaping optics 102 may create, for example, a beam having a vertical beam profile shaped as a Gaussian curve and a horizontal beam profile shaped as a relatively flat profile. For instance, in one embodiment, the beam shaping optics 102 may include a cylindrical lens and an acylindrical lens perpendicularly offset from one another such that a horizontal flat-top beam profile is generated. In another embodiment, a horizontal flat-top profile is created by beam shaping optics that includes a slit/obstruction that creates the desired profile. A horizontal flat-top beam profile may be desirable in certain applications, for example, to provide a wider fluid stream.

The lens 105 and the reflector 106 are provided between the ALL detector 107 and IAS detector 108. In the embodiment shown, the reflector 106 is positioned or otherwise shaped (e.g., with a hole or aperture in the center for axial light loss detection at ALL detector 107) to reflect IAS light perpendicularly to the IAS detector 107, which is positioned to receive the reflected light. It should be appreciated that in other embodiments, the reflector 106 is not present and the IAS detector is located proximate to the ALL detector 107 (i.e., not perpendicularly positioned).

Sample fluid is hydro-dynamically focused in a fluid sheath (e.g., injected into the center of the fluid sheath) past the interrogation zone 109 in the flow cell 104. A sheath fluid source, for example, may draw a sheath fluid used to hydro-dynamically focus the liquid sample. In one embodiment, the sheath fluid is water. The focused light beam from the beam shaping optics 102 is targeted at the interrogation zone 109 and irradiates the liquid sample at the interrogation zone 109. As sample cells or particles of interest intercept the light source, the light is scattered. The scattered light enters the lens 105 and is reflected by the reflector 106 (e.g., a holed-mirror), and received by the IAS detector 108. Thus, the IAS detector 108 may be used to measure intermediate angle scatter emitted from the liquid sample when the liquid sample is irradiated. Light that is not intercepted by cells or particles of interest pass through the lens 105 to the ALL detector 107. The ALL detector 107 may be used, for example, to measure axial light loss.

The IAS detector 108 is used to detect and measure intermediate angle scatter. In one embodiment, the IAS detector 108 includes a single detector that is used to detect intermediate angle scatter. In another embodiment, the IAS detector 108 is segmented and includes a plurality of detectors that are used as detection terminals to detect various angles of scattered. Example ranges of scatter light are 1 degree to 15 degrees, or narrowed to 2-10 degrees, or 3-7 degrees. For example, the IAS detector 108 may include more than one concentrically disposed detector ring. It should be appreciated that in other embodiments, one or more of the detectors of the plurality of detectors may have a shape other than a ring.

In one embodiment, the IAS detector includes two concentric detector rings. The first concentric detector ring may, for example, measure intermediate angle scatter between 2-7 degrees. The second concentric detector ring may, for example, measure intermediate angle scatter between 7-11 degrees. It should be appreciated that the angular ranges may vary in other embodiments.

It should also be appreciated that additional detectors may also be implemented. For example, in one embodiment, the IAS detector 108 includes a central detector that is concentrically disposed within the center of two or three concentric detector rings, such as the two detector rings described above for instance. In one embodiment, the central detector is also a concentric detector ring. It should be appreciated that the central detector may have different shapes other than a ring in other embodiments. For example, the central detector may be in the shape of a circle, square, rectangle, or other regular or irregular shape, and may preferably be large enough to accommodate the entire beam spot without the presence of a cell in the flow cell. In one embodiment, the central concentric detector ring measures intermediate angle scatter between approximately 2-5 degrees, another concentric detector ring measures intermediate angle scatter between approximately 5-7 degrees, and another concentric detector ring measures intermediate angle scatter between approximately 7-11 degrees.

It should be appreciated that in some embodiments, the angular ranges of the detectors may overlap. For example, the central concentric detector ring may measure intermediate angle scatter between approximately 2-6 degrees, the second concentric detector ring may measure intermediate angle scatter between approximately 5-7 degrees, and the third concentric detector ring may measure intermediate angle scatter between approximately 6-11 degrees.

In one embodiment, the system shown in FIG. 1 includes a mask 110 disposed across a portion of the IAS light detector 108 between the flow cell 104 and the IAS detector 108. The mask 110 is disposed between the flow cell 104 and the IAS light detector 108 and covers at least a central portion of the IAS detector so as to block diffraction patterns.

FIG. 2 illustrates a diagram of scattered light signals in the vertical and horizontal directions, according to one embodiment. The scatter signal 181 in the vertical direction at the detector 108 is a Gaussian curve and is shown to the right of IAS detector 108. The scatter signal 182 in the horizontal direction at the detector 108 is shown to the bottom of the IAS detector 108. The horizontal scatter signal 182 at the detector 108 resulting from a horizontal flat-top beam profile is corrupted/distorted and includes horizontal diffraction (or ripples) 190 in the signal.

The diffraction pattern (or ripples) 190 may be created by a mismatched index of refraction between the sheath fluid and the liquid sample, for example. Thus, the systems and methods provided in the present disclosure permits differences in refractive index between the sheath fluid and the liquid sample without corrupting the measurements for intermediate angle scatter with horizontal diffraction patterns. In this way, water may be used as the sheath fluid despite its difference in refractive index from the sample fluid. The sample fluid may comprise blood, for example, which has a different refractive index than water. For instance, the blood may include various cells, such as red blood cells, white blood cells, etc., and other particles that are detected. In some instances, the blood may be diluted with another liquid, such as water or diluent for example, but still have a sufficient difference refractive index than the sheath fluid, which creates diffraction or ripples in the intensity profile of the scattered light.

The diffraction pattern may also be created by the flat beam profile of the light beam. For example, the beam shaping optics may include a combination of lenses (e.g., one cylindrical lens and one acylindrical lens) configured to produce a horizontal flat-top beam profile at the point of intersection with the interrogation zone. The lenses used to form the flat beam profile may create horizontal diffraction patterns in the scatter signals at the IAS detector. In some instances, a flat-top beam profile may be formed by a slit positioned between the laser and the interrogation zone such that only light is passed through the slit. In such case, diffraction patterns are also created from the slit illumination and are present in the scatter signals at the IAS detector.

In one embodiment, as shown in FIG. 3, a mask 110 is disposed horizontally across a portion of the IAS detector 108 so as to block a horizontal diffraction pattern created by a horizontal flat-top beam profile and mismatched index of refraction between the sheath fluid and liquid sample. For instance, the mask 110 may be shaped approximately rectangular with the longitudinal axis extending horizontally.

In one embodiment, the mask 110 is disposed on the IAS detector 108. It should be appreciated that in other embodiments, the mask 110 may not necessarily be disposed on the IAS detector but sufficiently close to the IAS detector to accurately block the intended angular ranges of scattered light.

The mask 110 may be any type of material that sufficiently blocks light from being detected by the IAS detector 108. In one embodiment, the mask 110 is tape. In another embodiment, the mask 110 is an obstruction bar. The obstruction bar may be made of any variety of materials that block light, for instance a polymeric material. In yet another embodiment, the mask 110 is a photolithographic obstruction. In some instances, the mask 110 is made from a material that reflects light as well blocks light—e.g., a mirrored or reflective material.

In embodiments where the mask 110 is disposed on the IAS detector 108, it should be appreciated that mask should not be made of conductive materials such that the mask 110 will short the various detectors of the IAS detector 108.

In one embodiment, the mask 110 is an obstruction bar in the form of a holed mirror positioned to allow axial light loss measurements through a central hole in the obstruction bar, and redirect intermediate angle scatter from the flow cell 104 to the IAS detector 108.

In one embodiment, an obstruction bar is implemented in conjunction with a holed mirror that is positioned to allow axial light loss measurements through the central hole and redirect intermediate angle scatter. The obstruction bar is positioned next to the holed mirror, between the holed mirror and the IAS detector, such that a portion of the reflected intermediate angle scatter is blocked across a portion of the IAS detector (e.g., horizontally across the concentric rings of the IAS detector).

In one embodiment, the obstruction bar is in the form of a slotted mirror that includes reflective material to reflect intermediate angle scatter, but is slotted, however, to include an absence of reflective material so as to not reflect horizontal diffraction to the IAS detector. For example, the mirror may be shaped with a hole or cutout in the shape of slot that does not reflect light across a portion of the detector corresponding to where the horizontal diffraction would be present. The hole or cutout may be in the form of a rectangle slot, for instance, extending across a generally circular mirror (or two sides of a generally circular mirror), thus reflecting intermediate angle scatter but not reflecting light across a horizontal portion of the IAS detector that corresponds to where the horizontal diffraction is present.

FIG. 3 illustrates a diagram of a mask disposed on an IAS detector, according to one embodiment. As shown, mask 110 is disposed on IAS detector 108. The IAS detector 108 includes three concentrically disposed detector rings 201, 202, and 203. In the embodiment shown, the outer radius of the first concentric detector ring 201 is less than 4 mm; the inner radius and outer radius of the second concentric detector ring is approximately 4 mm and 7.6 mm, respectively; and, the inner radius and outer radius of the third concentric detector ring is approximately 9.6 mm and 13 mm, respectively.

Mask 110 is horizontally disposed across portions of all three concentric detector rings 201, 202, and 203 of IAS detector 108. In this way, the horizontal diffraction pattern is blocked by the mask 110 and not detected by any of the three concentric detector rings 201, 202, and 203. The dimensions of the mask 110 may vary but should be appropriately sized to sufficiently block the horizontal diffraction pattern. In one embodiment, the mask has a width of about 2mm. In another embodiment, the mask has a width ranging from 1-5 mm.

In some aspects of the present disclosure, an IAS detector is provided that is shaped and sized to receive a range of intermediate scatter excluding the horizontal diffraction. For example, the IAS detector may be a slotted detector or include two portions that are spaced apart from one another. FIG. 4 illustrates a slotted detector, according to one embodiment. The IAS detector 108 is slotted to include a first semi-circular half 108a and a second semi-circular half 108b spaced apart by a slot or gap 180. The slot or gap 180 shown is shaped and sized horizontally across the center of the IAS detector 108. The scatter signal 181 in the vertical direction at IAS detector 108 is a Gaussian curve as shown to the right of IAS detector 108, and scatter signal 182 in the horizontal direction at IAS detector 108 is shown to the bottom of the IAS detector 108. The horizontal scatter signal 182 is corrupted and includes horizontal diffraction 190 shown as ripples in the signal. The configuration of the IAS detector 108 of FIG. 4, wherein the horizontal diffraction is not detected because it falls within the slot 180 of IAS detector 108, thus avoids/ignores the detection of the horizontally distorted scatter signal at the IAS detector 108.

The flow cytometer system 100 may include other optical components that are not shown. For example, the system may include lenses and detectors for detecting fluorescent light, polarized side scatter, and/or depolarized side scatter. FIG. 1 primarily illustrates components for demonstrating forward scatter and intermediate angle scattering, and thus should not be construed as limiting.

The following paragraphs provide additional example embodiments for systems and methods of the present disclosure.

As stated above, in some aspects of the present disclosure, a flow cytometer system is provided. The system includes a flow cell for streaming a hydro-dynamically focused liquid sample past an interrogation zone, a light source positioned to irradiate the interrogation zone with a light beam, and beam shaping optics disposed between the light source and the flow cell. The beam shaping optics manipulates the light beam, and creates a horizontally flat beam profile that irradiates the liquid sample at the interrogation zone. The system includes an intermediate angle scatter (IAS) light detector positioned to measure intermediate angle scatter emitted from the liquid sample when the liquid sample is irradiated, and further includes a mask disposed horizontally across a portion of the IAS light detector, between the flow cell and the IAS light detector, and covering at least a central portion of the IAS light detector so as to block a horizontal diffraction pattern created by the flat beam profile irradiating the liquid sample.

In one embodiment, wherein the light source is a laser. In one embodiment, the system includes a sheath fluid source for drawing a sheath fluid used to hydro-dynamically focus the liquid sample. In some instances, the sheath fluid is water. In one embodiment, the mask is selected for a group consisting of: a tape, an obstruction bar, and a photolithographic obstruction. In one embodiment, the mask is an obstruction bar. In one embodiment, the obstruction bar is a holed mirror positioned to allow an axial light loss measurement through a central hole in the obstruction bar, and redirect intermediate angle scatter from the flow cell to the IAS light detector.

In one embodiment, the IAS light detector further includes two concentric detector rings. In some instances, the first detector ring measures intermediate angle scatter between about 2-7 degrees. In some instances, the second detector ring measures intermediate angle scatter between about 7-11 degrees.

In one embodiment, the two concentric detector rings includes a first concentric detector ring and a second concentric detector ring, and the IAS light detector further includes a central detector ring disposed concentrically within the first and second concentric detector rings. In some instances, the first concentric detector ring has an inner radius of approximately 4 mm and an outer radius of approximately 7.6 mm, and wherein the second concentric detector ring has an inner radius of approximately 9.6 mm and an outer radius of approximately 13 mm.

As stated above, in some aspects of the present disclosure, a flow cytometer system is provided. The system includes a flow cell for streaming a hydro-dynamically focused liquid sample past an interrogation zone, a sheath fluid source for drawing a sheath fluid used to hydro-dynamically focus the liquid sample, a light source positioned to irradiate the interrogation zone with a light beam, and beam shaping optics disposed between the light source and the flow cell. The sheath fluid is water, and the beam shaping optics manipulates the light beam. Further, the system includes an intermediate angle scatter (IAS) light detector positioned to measure intermediate angle scatter emitted from the liquid sample when the liquid sample is irradiated. Still further, the system includes a mask disposed across a portion of the IAS light detector, between the flow cell and the IAS light detector, and covering at least a central portion of the IAS light detector so as to block a diffraction pattern created by the sheath fluid when the liquid sample is irradiated.

In one embodiment, the light source is a laser. In one embodiment, the beam shaping optics create a horizontally flat beam profile that irradiates the liquid sample at the interrogation zone. In one embodiment, the mask is selected for a group consisting of: a tape, an obstruction bar, and a photolithographic obstruction. In one embodiment, the mask is an obstruction bar. In one embodiment, the obstruction bar is a holed mirror positioned to allow an axial light loss measurement through a central hole in the obstruction bar, and redirect intermediate angle scatter from the flow cell to the IAS light detector.

In one embodiment, the IAS light detector further comprises two concentric detector rings. In some instances, the first detector ring measures intermediate angle scatter between about 2-7 degrees. In some instances, the second detector ring measures intermediate angle scatter between about 7-11 degrees.

In one embodiment, the two concentric detector rings includes a first concentric detector ring and a second concentric detector ring, and the IAS light detector further includes a central detector ring disposed concentrically within the first and second concentric detector rings. In some instances, the first concentric detector ring has an inner radius of approximately 4 mm and an outer radius of approximately 7.6 mm, and wherein the second concentric detector ring has an inner radius of approximately 9.6 mm and an outer radius of approximately 13 mm.

As stated above, in some aspects of the present disclosure, a system is provided for blocking a diffraction pattern created by (1) a flat laser beam profile irradiating a flow cytometer liquid sample or (2) a mismatched index of refraction between a sheath fluid and a liquid sample in a flow cytometer. The system includes an intermediate angle scatter (IAS) light detector positioned to measure intermediate angle scatter emitted from the liquid sample when the liquid sample is irradiated, and a mask disposed across a portion of the IAS light detector and covering at least a central portion of the IAS light detector so as to block a diffraction pattern.

In one embodiment, the mask is disposed horizontally across the IAS light detector. In one embodiment, the mask is selected for a group consisting of: a tape, an obstruction bar, and a photolithographic obstruction. In one embodiment, the mask is an obstruction bar. In one embodiment, the obstruction bar is a holed mirror positioned to allow an axial light loss measurement through a central hole in the obstruction bar, and redirect intermediate angle scatter from the flow cell to the IAS light detector.

In one embodiment, the IAS light detector further comprises two concentric detector rings. In some instances, the first detector ring measures intermediate angle scatter between about 2-7 degrees. In some instances, the second detector ring measures intermediate angle scatter between about 7-11 degrees.

In one embodiment, the two concentric detector rings includes a first concentric detector ring and a second concentric detector ring, and the IAS light detector further includes a central detector ring disposed concentrically within the first and second concentric detector rings. In some instances, the first concentric detector ring has an inner radius of approximately 4 mm and an outer radius of approximately 7.6 mm, and wherein the second concentric detector ring has an inner radius of approximately 9.6 mm and an outer radius of approximately 13 mm.

In one embodiment, there is provided a flow cytometer having a flow cell for streaming a hydro-dynamically focused liquid sample past an interrogation zone, a sheath fluid source for drawing a sheath fluid used to hydro-dynamically focus the liquid sample, a light source positioned to irradiate the interrogation zone with a light beam, and beam shaping optics disposed between the light source and the flow cell. The sheath fluid is water, and the beam shaping optics to manipulates the light beam. Further, the system includes an intermediate angle scatter (IAS) light detector positioned to measure intermediate angle scatter emitted from the liquid sample when the liquid sample is irradiated. Still further, the system includes a mask disposed across a portion of the IAS light detector, between the flow cell and the IAS light detector, and covering at least a central portion of the IAS light detector so as to block a diffraction pattern created by the sheath fluid when the liquid sample is irradiated.

In another embodiment, there is provided a system for blocking a diffraction pattern created by (1) a flat laser beam profile irradiating a flow cytometer liquid sample or (2) a mismatched index of refraction between a sheath fluid and a liquid sample in a flow cytometer. The system includes an intermediate angle scatter (IAS) light detector positioned to measure intermediate angle scatter emitted from the liquid sample when the liquid sample is irradiated, and a mask disposed across a portion of the IAS light detector and covering at least a central portion of the IAS light detector so as to block a diffraction pattern.

As stated above, in some aspects of the present disclosure, a method of configuring a flow cytometer to block a diffraction pattern created by (1) a flat laser beam profile irradiating a flow cytometer liquid sample, or (2) a mismatched index of refraction between a sheath fluid and a liquid sample in a flow cytometer, is provided. The method includes positioning a mask across a portion of an intermediate angle scatter (IAS) light detector, which is positioned to measure intermediate angle scatter emitted from the liquid sample when the liquid sample is irradiated. The mask covers at least a central portion of the IAS light detector so as to block a diffraction pattern.

In yet another embodiment, there is provided a method of configuring a flow cytometer to block a diffraction pattern created by (1) a flat laser beam profile irradiating a flow cytometer liquid sample, or (2) a mismatched index of refraction between a sheath fluid and a liquid sample in a flow cytometer, is provided. The method includes positioning a mask across a portion of an intermediate angle scatter (IAS) light detector, which is positioned to measure intermediate angle scatter emitted from the liquid sample when the liquid sample is irradiated. The mask covers at least a central portion of the IAS light detector so as to block a diffraction pattern.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example.

It should be understood that some of the techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The preceding examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

That which is claimed is:

1. A flow cytometer system for blocking a diffraction pattern, the system comprising:
   an intermediate angle scatter (IAS) light detector; and
   a mask disposed across a portion of the IAS light detector and covering at least a central portion of the IAS light detector so as to block a diffraction pattern created by:
   (1) a flat beam profile irradiating the liquid sample while allowing all IAS signals to be detected by the IAS light detector; or
   (2) a mismatched index of refraction between a sheath fluid and a liquid sample when the liquid sample is irradiated while allowing all IAS signals emitted from the liquid sample to be detected by the IAS light detector.

2. The flow cytometer system of claim 1, wherein the IAS light detector is positioned to measure intermediate angle scatter signals emitted from the liquid sample when the liquid sample is irradiated.

3. The flow cytometer system of claim 1, wherein the mask comprises a central hole.

4. The flow cytometer system of claim 3, wherein the central hole is positioned to allow one or more axial light loss (ALL) measurements through the central hole.

5. The flow cytometer system according to claim 3, wherein the central hole in the mask has a radius of up to 4 mm.

6. The flow cytometer system of claim 1, wherein the mask is disposed horizontally across the IAS light detector.

7. The flow cytometer system of claim 1, wherein the mask is selected from the group consisting of: a tape, an obstruction bar, and a photolithographic obstruction.

8. The flow cytometer system of claim 7, wherein the mask is an obstruction bar.

9. The flow cytometer system of claim 8, wherein the obstruction bar is a holed mirror positioned to allow an axial light loss measurement through a central hole in the obstruction bar and to redirect intermediate angle scatter to the IAS light detector.

10. The flow cytometer system of claim 1, wherein the IAS light detector further comprises a first concentric detector ring and a second concentric detector ring.

11. The flow cytometer system of claim 10, wherein the first detector ring measures intermediate angle scatter signals between about 2-7 degrees.

12. The flow cytometer system of claim 10, wherein the second detector ring measures intermediate angle scatter signals between about 7-11 degrees.

13. The flow cytometer system of claim 10, wherein the two concentric detector rings comprise a first concentric detector ring and a second concentric detector ring, and wherein the IAS light detector further comprises a central detector ring disposed concentrically within the first and second concentric detector rings.

14. The flow cytometer system of claim 13, wherein the first concentric detector ring has an inner radius of approximately 4 mm and an outer radius of approximately 7.6 mm, and wherein the second concentric detector ring has an inner radius of approximately 9.6 mm and an outer radius of approximately 13 mm.

15. A method of configuring a flow cytometer to block a diffraction pattern, the method comprising:
    positioning a mask across a portion of an intermediate angle scatter (IAS) light detector configured to measure IAS signals, wherein the mask covers at least a central portion of the IAS light detector so as to block a diffraction pattern; and
    detecting all IAS signals emitted from a flow cytometer liquid sample by the IAS light detector while allowing all IAS to be detected by the IAS light detector.

16. The method of claim 15, wherein the diffraction pattern is created by:
    (1) a flat laser beam profile irradiating a flow cytometer liquid sample; or
    (2) a mismatched index of refraction between a sheath fluid and a liquid sample in the flow cytometer.

17. The method of claim 15, wherein the IAS detector is positioned to measure intermediate angle scatter signal emitted from the liquid sample when the liquid sample is irradiated.

18. The method of claim 15, wherein the mask comprises a central hole.

19. The method of claim 18, wherein the central hole is positioned to allow one or more axial light loss (ALL) measurements through the central hole.

20. The method of claim 18, wherein the central hole in the mask has a radius of up to 4 mm.

* * * * *